United States Patent [19]
Netti et al.

[11] Patent Number: 5,888,530
[45] Date of Patent: Mar. 30, 1999

[54] METHOD OF ENHANCING DELIVERY OF A PHARMACEUTICAL FORMULATION

[75] Inventors: Paolo Netti; Rakesh K. Jain, both of Boston, Mass.

[73] Assignee: The General Hospital Corporation, Boston, Mass.

[21] Appl. No.: 683,083

[22] Filed: Jul. 18, 1996

Related U.S. Application Data

[60] Provisional application No. 60/001,362, Jul. 21, 1995.

[51] Int. Cl.$^6$ .................................................. A61F 2/02
[52] U.S. Cl. .................................................... 424/423
[58] Field of Search .......................................... 424/423

[56] References Cited

U.S. PATENT DOCUMENTS

| | | |
|---|---|---|
| 4,846,792 | 7/1989 | Bobo, Jr. et al. . |
| 5,229,131 | 7/1993 | Amidon et al. ................ 424/451 |
| 5,380,273 | 1/1995 | Dubrul et al. . |
| 5,386,837 | 2/1995 | Sterzer . |
| 5,396,897 | 3/1995 | Jain et al. . |
| 5,403,590 | 4/1995 | Forse . |

FOREIGN PATENT DOCUMENTS

| | | |
|---|---|---|
| 0402964 A1 | 12/1990 | European Pat. Off. . |
| 0512285 A1 | 11/1992 | European Pat. Off. . |

OTHER PUBLICATIONS

Suzuki et al. (1981) *JNCI* 67:663–669.
Jain (1994) *Scientific American* 271:58–65.
Netti et al. (1995) *Cancer Res.* 55:5451–5458.
Hori et al. (1994) *Microvascular Research* 48:246–256.
Thompson, et al "Tumor Detection using . . . " IEEE International Microwave Symposium Digest, pp. 39–44 (1979).
Fadnes, et al "Interstitial Fluid Pressure in Rats Measured with a Modified Wick Technique" Microvascular Res. vol. 14, pp. 27–36, (1977).
Boucher, et al., Interstitial Pressure Gradients in Tissue–isolated and Subcutaneous Tumors: Implications for Therapy, Cancer Res. vol. 50, pp. 4478–4484, Aug. 1, 1990.
Young, et al., "The Significance of the Tissue Pressure of Normal Testicular and of Neoplastic (Brown–Pearce Carcinoma) Tissue in the Rabbit", J. Path.Bact.vol. LXII, pp. 313–333.
Boucher et al, "Interstitial Hyprtension in Superficial Metastatic Melanomas in Humans", Cacner Res. vol. 51, pp. 6691–6694, Nov. 8, 1991.
Roh, et al, "Interstital Hypertension in Carcinoma of Uterine Cervix in Patients: Possible Correlation with Tumor Oxygenation and Radiation Response", Cancer Res. vol. 51, pp. 6695–6698, Nov. 8, 1991.
Kopans, et al, "A Modified Needle–Hookwire Technique to Simplify Preoperative Localization of Occult Breast Lesions", Radiology, vol. 134, p. 781, 1980.
Meyer, et al, "Preoperative Roentgenographically Guided Guided Percutaneous Localization of Occult Breast Lesions", Arch. Surg., vol. 117, pp. 65–68, Jan. 1982.
Baum, T.D. et al, J. Surg. Res. 48:629–634, (1990).
Frankel J.P. et al, J. Neurosurg. and Psychiatry 53:96–101, (1990).
Baptista, R.I. et al Am. Pharmacol. 23:59–62 (1989).
Frank W. et al, Clin. Pharmacol Ther. 46(2):214–239 (1989).
Rovers, J.P. et al, Crit. Care Med. 17(8):814–821 (1989).

(List continued on next page.)

*Primary Examiner*—Carlos A. Azpuru
*Attorney, Agent, or Firm*—Lappin & Kushmer LLP

[57] ABSTRACT

The invention provides a method of enhancing the amount of a pharmaceutical composition delivered to a target tissue site in a mammal, by creating a transient differential between tile hydrostatic pressure in the target site and a region near the target tissue site whereby the composition is transported toward the site. An apparatus for performing the method is provided. In one form that apparatus includes a pharmaceutical reservoir, pump, and an agent reservoir and pump.

38 Claims, 1 Drawing Sheet

OTHER PUBLICATIONS

Benovic, J.L. et al, Am. Rev. Cell Biol. 4:405–428 (1988).
Miska, P.T. et al, J. Heart Transplant 7(5):353–355, (1988).
Hola, E.T. et al, Am. J. Hosp. Pharm. 43:2474–2478 (1986).
Colangello, A. et al, Am. J. Hosp. Pharm. 42:581–584 (1985).
Lefkowitz, R.J. et al, Curr. Top Cell Regul. 127:205–230 (1980).
Belehradek, et al, Abstract "Electrochemotherapy, a New Antitumor Treatment".
Mir, et al, Abstract, "Local and Systematic Antitumor Effects in Mice of the Combination of Electrochemotherapy and an immunotherpay".
Roh, et al., "Interstitial Hypertension in Carcinoma of Uterine Cervix in Patients: Possible Correlation with Tumor Oxygenation and Radiation Response", Cancer Res., vol. 51, pp. 6695–6698, Nov. 8, 1991.
Kopans, et al., A Modified Needle–Hookwire Technique to Simplify Preoperative Localization of Occult Breast Lesions, Arch Surg., vol. 134, p. 781, 1980.
Meyer, et al., "Preoperative Roentgenographically Guided Percutaneous Localization of Occult Breast Lesions", Arch. Surg., vol. 117, pp. 65–68, Jan. 1992.
Baum, T.D. et al. (1990) J. Surg. Res. 48:629–634.
Frankel, J.P. et al., (1990) J. Neurosurg and Psychiatry 53:96–101.
Baptista, R.I. et al. (1989) Am Pharmacol. 23:59–62.
Frank W. et al., (1989) Clin. Pharmacol Ther. 46(2) 234–239.
Rovers, J.P. et al. (1989) Crit. Care Med. 17(8):814–821.
Benovic, J.L. et al. (1988) Arm Rev. Cell Biol. 4:405–428.
Miska, P.T. et al. (1988) J. Heart Transplant 7(5):353–355.
Hola E.T. et al. (1986) Am. J. Hosp. Pharm. 43:2474–2478.
Colangello A. et al. (1985) Am J. Hosp. Pharm. 42:581–584.
Lefkowitz R.J. et al. (1980) Curr. Top Cell, Regul. 127:205–230.

METHOD OF ENHANCING DELIVERY OF A PHARMACEUTICAL FORMULATION

This invention was partially funded by the National Institutes of Health (grant number CA-56591). The Government has certain rights in the invention.

This application is a continuation-in-part of copending provisional application U.S. Ser. No. 60/001,362, filed Jul. 21, 1995.

FIELD OF THE INVENTION

The present invention relates to the field of delivery of diagnostic and therapeutic agents, and more specifically to enhancement of delivery of a pharmaceutical formulation to a target tissue site in a mammal.

BACKGROUND OF THE INVENTION

A major factor in determining the efficacy of an intravenously-administered diagnostic or therapeutic agent is the efficiency with which the agent will be delivered to its target tissue site. For a variety of reasons, the amount of a therapeutic agent which actually penetrates the target tissue site is likely to be less than the amount of agent which was injected. Inefficient penetration of an agent into the target tissue results in the need for higher dosages of the therapeutic agent to obtain maximum therapeutic benefit at the target site, creating an increased risk of agent-induced toxicity in non-target tissues.

This problem is particularly pronounced in relation to delivery of therapeutic or diagnostic agents to malignant growths such as solid tumors. The cancerous cells of solid tumors often occupy less than half the volume of the tumor. A highly disorganized system of blood vessels weaves through the tumor mass, contributing from one to ten percent of the total tumor volume. A collagen-rich matrix known as the interstitium surrounds the cancer cells, filling the remaining space between the cells and the tumor vasculature. Plasmatic fluid can extravasate in the interstitium driven by an hydrostatic and oncotic pressure gradient. The absence of a well-defined lymphatic system in the tumor mass leads to an accumulation of these fluids in the interstitium. This accumulation leads to an increase in interstitial fluid pressure (Boucher, Y. Baxter, L. T., and Jain, R. K. (1990) *Cancer Res.* 50, 4478–4484). The interstitial pressure in a tumor is uniformly elevated and is approximately equal to the microvascular pressure (Boucher, Y. and Jain, R. K. (1992) *Cancer Res.* 52, 5110–5114). This lack of pressure differential impedes movement of a therapeutic agent into the tumor interstitium from the tumor vasculature.

One way to overcome the barrier created by the elevated pressure is to increase the difference between the microvascular pressure and interstitial pressure, either by increasing microvascular pressure or by lowering interstitial pressure. An increase of tumor microvascular pressure can be pursued by systemic infusion of vasoactive agents (Zlotecki R. A., Boucher Y., Lee I., Baxter, L. T., and Jain R. K. (1993) *Cancer Res.* 53, 2466–2468, and Ziotecki R. A., Baxter, L. T., Boucher Y., and Jain R. K. (1995) *Microvascular Res.*, in press). Unfortunately, the increase in microvascular pressure is rapidly followed by a corresponding increase in interstitial pressure. The time required for the new equilibration between microvascular pressure and interstitial pressure is too short to induce any appreciable increase of macromolecular uptake, following a single or continuous injection of vasoactive agents.

A number of other efforts have been made to increase the efficiency of therapeutic agent delivery to tumors. For example, angiotensin II, a hypertension-inducing agent, has been administered at a constant dosage in combination with therapeutic agents. Other agents such as dexamethasone, indomethasin, and ketanserin have been co-administered at constant dosages with chemotherapeutic agents. In spite of these efforts, delivery of therapeutic agents to tumors remains inefficient, and further improvements are needed to optimize dosages and consequently to minimize toxicities of these agents.

SUMMARY OF THE INVENTION

The present inventors have discovered that delivery of a therapeutic or diagnostic agent to a target tissue site in a mammal can be significantly enhanced by creating a repetitive, transient pressure differential between the target tissue site and a region near the target tissue site. The pressure differential may be created by physical means or by use of an agent capable of modulating the hydrostatic pressure within the mammal. In accordance with the invention, agents capable of modulating the hydrostatic pressure within the mammal may be delivered to the region near the target tissue site systemically, e.g., by intravenous injection. An agent capable of modulating hydrostatic pressure in accordance with the invention may act by increasing the hydrostatic pressure at the region near the target tissue site, or by decreasing the hydrostatic pressure at the target tissue site. Following the induced change in pressure, the resultant pressure differential dissipates as the system equilibrates. During the time the differential pressure is non-zero, the pressure gradient between the adjacent region and the target tissue site is effective to establish a convective transport of the therapeutic or diagnostic agent from the adjacent region of relatively high pressure toward the region of relatively low pressure, including the target tissue site.

In one embodiment, the invention provides a method of enhancing delivery of a pharmaceutical formulation to a target tissue site in a mammal, comprising the steps of: delivering the pharmaceutical formulation to the mammal at a region near the target tissue site; establishing a repetitive pulsatile pressure increase at the region, thereby establishing a transient repetitive pulsatile pressure differential between the region and the target tissue site, and in response thereto, transport of said pharmaceutical formulation from the region toward the target tissue site. The transport may be primarily convective in response to the pressure differential. The repetition rate may be constant (i.e. periodic) or irregular.

Alternatively, the pressure differential may be accomplished by establishing a repetitive pulsatile pressure decrease at the target tissue site, rather than an increase at the region surrounding the target tissue site, or combinations may be used.

In another form, the invention provides an apparatus for administering a pharmaceutical formulation to a tissue site in a mammal, comprising: a first reservoir for storing the pharmaceutical formulation; a second reservoir for storing an agent capable of establishing an increase in hydrostatic pressure in the mammal at the locus of the agent in the mammal; an agent pump for delivering the agent from the second reservoir to a region near the tissue site on a repetitive pulsatile basis; and a pharmaceutical formulation pump for delivering the pharmaceutical formulation from the first reservoir to the region. In accordance with the invention, the apparatus may deliver the pharmaceutical formulation and the hydrostatic pressure agent by systemic intravenous injection.

BRIEF DESCRIPTION OF THE DRAWING

The foregoing and other objects of the invention, the various features thereof, as well as the invention itself, may be more fully understood from the following description, when read together with the accompanying drawing in which.

DESCRIPTION OF THE PREFERRED EMBODIMENTS

Figure 1:
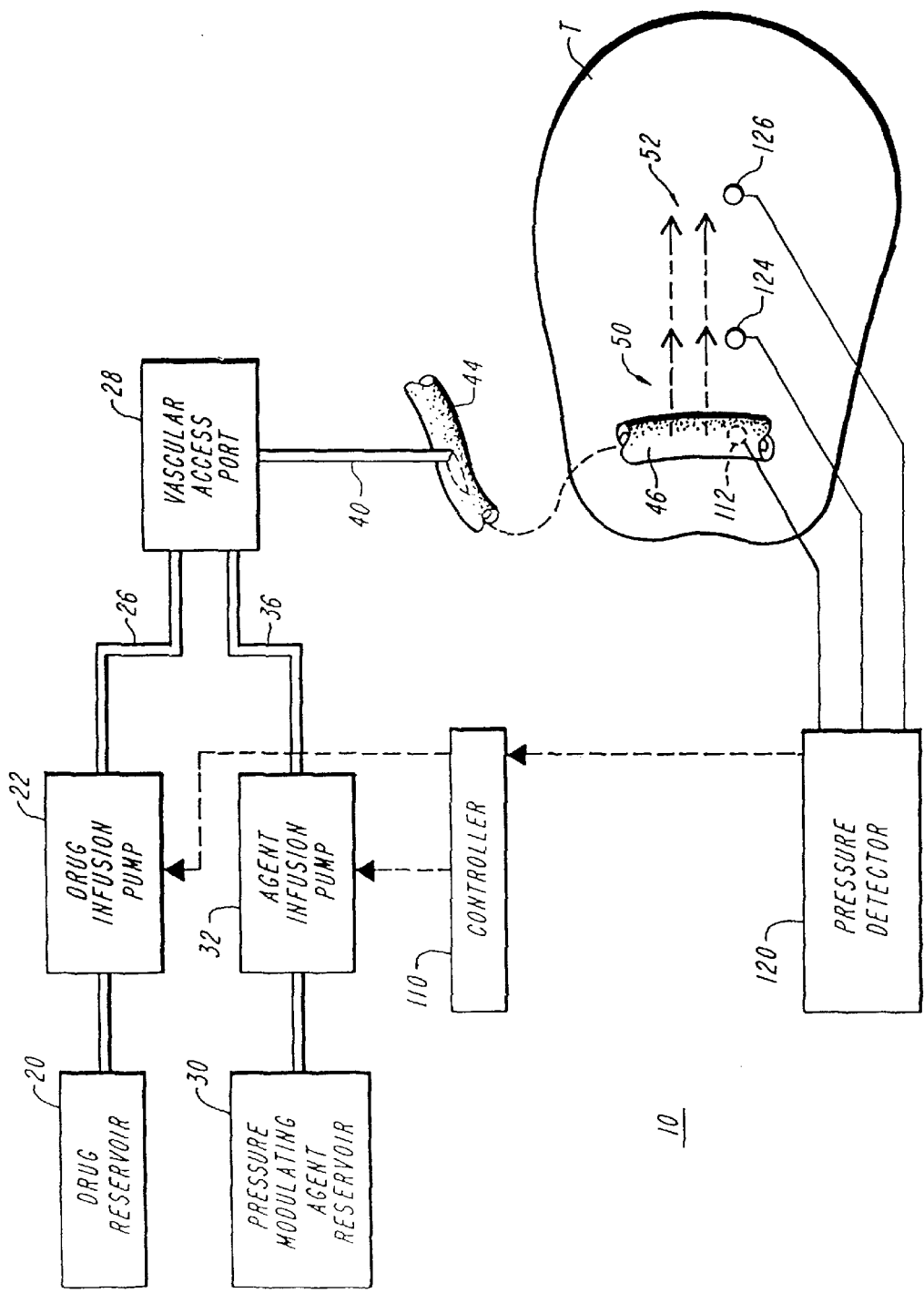
FIG. 1 shows the apparatus of the invention.

By mathematically modeling fluid transport in solid tumors, the present inventors have shown that interstitial pressure can be modulated by two distinct mechanisms: (a) by fluid exchange across tumor vessel wall and (b) by fluid percolation through the extracellular matrix (Netti P. A. et al., (1995) *Cancer Res.* 55, 5451–5458). The model predictions have been successfully tested experimentally. During a change in blood pressure, the predominant fluid transport mechanism is the extravasation across the vascular wall. This phenomenon occurs in a time scale of the order of 10 seconds, and is independent of the tumor size. The present inventors' calculations show that single increase of systemic pressure, which is currently under clinical trials in Japan (Hori K., et al. (1985) *J. Natl. Canc. Inst.* 74, 453–459; Hori K., et al. (1993) *Cancer Res.* 53, 5528–5534), does not lead to an appreciable improvement of uptake of the therapeutic agent.

However, periodic modulation of the microvascular pressure or of the hydrostatic pressure of the target tissue site results in a plurality of additive, incremental increases in convective transport of the therapeutic agent into the target tissue site. The target tissue site and the microvasculature supplying the target tissue site initially have a characteristic baseline hydrostatic pressure which is at a first equilibrium value. When the microvascular pressure is modulated, a transient increase to a second equilibrium value is created in the microvascular pressure. After a time lag, the hydrostatic pressure of the target tissue site also increases to the second equilibrium value. During this time lag, an increased amount of the therapeutic agent moves out of the microvasculature and into the target tissue site. When the hydrostatic pressure of the target tissue site reaches the second equilibrium value, the microvascular pressure and the hydrostatic pressure of the target tissue site are allowed to return to their first, baseline, equilibrium value, and when this occurs, another transient increase in microvascular pressure is induced. The hydrostatic pressure of the target tissue site will again increase to the second equilibrium value with the concomitant increase in convective transport of the therapeutic agent out of the microvasculature. The cycle is repeated periodically to modulate a repeated, transient pressure differential between the target tissue site and its surrounding microvasculature.

Similar incremental increases in therapeutic agent transport out of the microvasculature may be effected by inducing a series of transient decreases in the hydrostatic pressure of the target tissue site.

In accordance with the method of the invention, therefore, transport of a pharmaceutical formulation toward a target tissue site is increased by the creation of a transient, repetitive pulsatile pressure differential between the microvasculature at a region near the target tissue site and the target tissue site. This pressure differential is established by inducing a repetitive pulsatile increase in hydrostatic pressure in the region near the target tissue site, or by inducing a periodic pulsatile decrease in the hydrostatic pressure at the target tissue site. The pressure differential may be induced systemically, e.g., by intravenous injection of agents capable of mediating transient pressure differentials via the microvasculature surrounding the target tissue site. Any tissue site may be targeted in accordance with the invention: for example, the target tissue site may be any solid tumor, either within an organ (such as metastasis within a lymph node) or a solid tumor which exists independent of an organ.

In accordance with the present invention the microvascular pressure of the target tissue site may be measured using known methods. For example, the microvascular pressure may generally be estimated by measuring the blood pressure of the mammal. The hydrostatic pressure of the target tissue site may be measured by inserting a needle into the target tissue site, the needle being filled with physiological saline and coupled to a pressure measuring device (Boucher, Y. et al. (1990), supra). Alternatively, the hydrostatic pressure of the target tissue site may be measured using the wick-in-needle method, in which fibers of polyester or other multifilamentous material is placed within the lumen of the needle to provide a large surface area continuum with the target tissue site and to reduce occlusion. A third method of measuring the hydrostatic pressure at the target tissue site employs a micropipet connected to a servo null pressure-measuring system as disclosed in Boucher, Y. et al. (1990), supra. All of these methods for measuring hydrostatic pressure of a target tissue site are described more fully in U.S. Pat. No. 5,396,897, incorporated herein by reference.

The optimum repetition rate of the pulsatile pressure differential is related to the time required for equilibration between the blood pressure of the microvasculature near the target tissue site and the hydrostatic pressure that characterizes the target tissue site. The repetition rate of the pulsatile pressure differential may be constant or irregular, and may be determined by a feedback mechanism capable of continuously measuring and comparing blood pressure of the microvasculature near the target tissue site and the hydrostatic pressure of the target tissue site. Alternatively, the repetition rate may be fixed at a specified constant value. In accordance with the invention, delivery of the pharmaceutical formulation may occur simultaneously with induction of the repetitive pulsatile pressure differential and such delivery may occur through systemic intravenous injection. The pharmaceutical formulation may be administered at a constant dosage or in a pulsatile manner which is synchronous with the repetitive pulsatile pressure differential.

The repetitive pulsatile pressure differential may be induced by any means. For example, the pulsatile pressure differential is induced by mechanical means. More preferably, the pulsatile pressure differential is induced by chemical means, for example, by intravenous infusion of a pressure modulating agent, that is, an agent which is capable either of establishing a transient increase in hydrostatic pressure in the mammal at the region near the target tissue site, or of establishing a transient decrease in the hydrostatic pressure of the target tissue site. When the target tissue site is a solid tumor or a lymph node, a repetitive pulsatile pressure increase may be induced at a region near the target tissue site by a pressure modulating agent such as angiotensin II, epinephrine, norepinephrine, and the like. Alternatively, a repetitive pulsatile pressure decrease may be induced at the target tissue site by a tumor interstitial pressure modulating agent such as an agent that destroys the interstitial matrix such as hyaluronidase.

A therapeutic or diagnostic agent administered in accordance with the method of the invention will be in the form of a pharmaceutical formulation, that is, a therapeutically effective amount of a therapeutic or diagnostic agent, hereinafter the active ingredient, in the formulation is combined with a pharmaceutically acceptable carrier. Delivery of any pharmaceutical formulation to any target tissue site may be enhanced using the method of the invention. Preferably, the tissue site targeted is a solid tumor. In accordance with the method of the invention, the pharmaceutical formulation is administered to the mammal at a region near the target tissue site. As defined herein, a region near the target tissue site includes at least the microvasculature which supplies the target tissue site, and may additionally include non-target tissue that surrounds or is near the target tissue site. When the target tissue is a tumor, the region near the target tissue site may include the tumor microvasculature and the peri-tumor region. If the tumor is located within an organ, the region near the target tissue site may include the entire organ. For example, when the target tissue is located within a lymph node, the region near the target site may include the entire lymph node. The region near the target tissue site may be intravascular, establishing enhanced transport of the formulation across the wall of the blood vessels and then further toward the target tissue site. Alternatively, the region may be extravascular, so that formulation at the region is transported toward the target tissue site.

In accordance with the invention, "a therapeutically effective amount" of a therapeutic agent is defined as an amount of each active component of the pharmaceutical formulation that is sufficient to show a meaningful patient benefit, i.e., to cause a decrease in or amelioration of the symptoms of the condition being treated, as determined by the attending physician. When the pharmaceutical formulation comprises a diagnostic agent, "a therapeutically effective amount" is defined as an amount of each active component of the pharmaceutical formulation that is sufficient to produce an image or other diagnostic parameter in the diagnostic system employed. When applied to an individual active ingredient, administered alone, the term refers to that ingredient alone. When applied to a combination of active ingredients, the term refers to combined amounts of the active ingredients that result in the therapeutic effect, whether administered in combination, serially or simultaneously. Effective amounts of the pharmaceutical formulation will vary according to factors such as the degree of susceptibility of the individual, the age, sex, and weight of the individual, and idiosyncratic responses of the individual.

The term "pharmaceutically acceptable" means a non-toxic material that does not interfere with the effectiveness of the biological activity of the active ingredient(s). A pharmaceutical formulation administered in accordance with the invention may contain, in addition to the active ingredient(s), a pharmaceutically acceptable carrier, As used herein "pharmaceutically acceptable carrier" includes any and all solvents, dispersion media, coatings, antibacterial and antifungal agents, isotonic agents, absorption delaying agents, diluents, fillers, salts, buffers, stabilizers, solubilizers, and other materials well known in the art. The characteristics of the carrier will depend on the route of administration.

A pharmaceutical formulation in accordance with the present invention preferably comprises one or more therapeutic or diagnostic agents which may act by incorporation into actively dividing cells, by interacting with cells bearing a particular surface determinant, by specifically targeting malignant cells within the tumor, and the like. Many such therapeutic and diagnostic agents are known: for example, such agents include cytotoxic chemotherapeutic drugs, including but not limited to tumor antigen specific monoclonal antibodies which may optionally be attached to an effector molecule such as a toxin, a radionuclide, an enzyme, a hapten, and the like. In accordance with the invention, diagnostic agents include imaging agents such as radionuclides, which may optionally be attached to a targeting molecule such as a tumor-specific monoclonal antibody. The method of the invention may also be used in combination with gene therapy methods, for example, in those therapies which employ a gene such as thymidine kinase introduced into tumor cells to induce sensitivity to an active ingredient such as acyclovir. The method of the invention may also be used after chemotherapy to enhance delivery of a cytokine or interleukin to hematopoeitic cells.

Supplementary active compounds, such as adjuvants, cytokines, lymphokines, hematopoietic factors, thrombolytic factors, and the like, can also be incorporated into the pharmaceutical formulation administered in accordance with the method of the invention. Adjuvant is used in its broadest sense and includes any immune stimulating compound such as an interferon or such as immune stimulating interleukins, for example, interleukin-4, interleukin-10, interleukin-12, and the like. Adjuvants contemplated herein include resorcinols, non-ionic surfactants such as polyoxyethylene oleyl ether and n-hexadecyl polyethylene ether. Cytokines, lymphokines, and hematopoietic factors which may be included in pharmaceutical formulations administered using the method of the invention include, for example, macrophage-colony stimulating factor (M-CSF), granulocyte-macrophage colony stimulating factor (GM-CSF), granulocyte colony stimulating factor (G-CSF), erythropoietin, interleukins such as IL-1, IL-2, IL-3, IL-5, IL-6, IL-7, IL-8, IL-9, IL-11, IL-13, and the like.

The pharmaceutical formulation of the invention may be in the form of a liposome in which the active ingredient(s) are combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

The pharmaceutical formulation may be administered in any convenient manner such as by injection (subcutaneous, intravenous, intramuscular, intraperitoneal, or the like), oral administration, sublingual administration, inhalation, transdermal application, or rectal administration. When a pharmaceutical formulation is administered orally in accordance with the method of the invention, the formulation will be in the form of a tablet, capsule, powder, solution or elixir. When administered in tablet form, the pharmaceutical formulation may additionally contain a solid carrier such as a gelatin or an adjuvant. The tablet, capsule, and powder contain from about 5 to 95% active ingredient(s), and preferably from about 25 to 90% active ingredient(s). When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the active ingredient(s) and preferably from about 1 to 50% active ingredient(s). When a pharmaceutical formulation is administered by intravenous, cutaneous or subcutaneous injection in accordance with the present invention, the formulation will be in the form of a pyrogen-free, parenterally acceptable aqueous solution. The preparation of such parenterally acceptable solutions, having due regard to pH, isotonicity, stability, and the like, is within the skill in the art. A preferred pharmaceutical formulation for intravenous, cutaneous, or subcutaneous injection should contain, in addition to the active ingredient(s) an isotonic vehicle such as Sodium Chloride Injection, Ringer's Injection, Dextrose Injection, Dextrose and Sodium Chloride Injection, Lactated Ringer's Injection, or other vehicle as known in the art. A pharmaceutical formulation administered in accordance with the method of the invention may also contain stabilizers, preservatives, buffers, antioxidants, or other additives known to those of skill in the art.

The amount of pharmaceutical formulation comprising a therapeutic agent which is administered to a mammal or patient in accordance with the method of the present invention will depend upon the nature and severity of the condition being treated, and on the nature of prior treatments which the patient has undergone. Initially, the attending physician will administer low doses of the active ingredient (s) and observe the patient's response. Larger doses of the active ingredient(s) may be administered until the optimal therapeutic effect is obtained for the patient, and at that point the dosage is not increased further. The duration of therapy using the method of the present invention will vary, depending on the severity of the disease being treated and the condition and potential idiosyncratic response of each individual patient. Ultimately the attending physician will decide on the appropriate amount and duration of therapy using a pharmaceutical composition in accordance with the method of the present invention.

The method of the invention may also be used to enhance delivery of a diagnostic agent to a target tissue site. Delivery of any diagnostic agent may be enhanced in accordance with the present invention. For example, delivery of a labeled diagnostic agent such as an antibody specific for the target tissue site, a labeled binding substance such as a ligand specific for a receptor present at the target tissue site, an isotope which specifically accumulates at the target tissue site, and the like, may be enhanced using the method of the invention. Any label may be present on the diagnostic agent, for example, the diagnostic agent may be isotopically labeled, fluorescently labeled, enzymatically labeled, chemically labeled (as in a label which is detected calorimetrically), chemiluminescently labeled, spin labeled, and the like. As set forth above, the diagnostic agent will be administered as a pharmaceutical formulation.

An exemplary administration system 10 embodying the invention is shown in FIG. 1. System 10 includes a therapeutic or diagnostic (T/D) agent reservoir 20 and associated infusion pump 22 coupled via a catheter 26 to a vascular access port 28, and includes a hydrostatic pressure modulating (P/M) agent reservoir 30 and associated infusion pump 32 coupled via a catheter 36 to the vascular access port 28. The port 28 is coupled via a catheter 40 to blood vessel 44 of the vascular system of a mammal requiring treatment. The vessel 44 is coupled via the vascular system to blood vessel 46, which is at a local region 50 in the mammal near a target tissue site 52. In the illustrated embodiment the vessel 46, local region 50 and target tissue site 52 all are located within a tumor T.

The T/D agent reservoir 20 and pump 22, P/M agent reservoir 30 and pump 32, access port 28 and catheters 26 and 36, may all be contained within a single biocompatible housing which is implanted, along with the catheter 40, in the mammal receiving treatment. Alternatively, the T/D agent reservoir 20 and pump 22 and P/M agent reservoir 30 and pump 32 may remain outside the body of the mammal, with only vascular access port 28 and its output catheter 40 being implanted in the mammal's body. The respective pumps may be programmed to perform a predetermined pulsatile infusion of the contents of the respective reservoirs 20 and 30 to the vessel 44 and thus to the vessel 46.

In one form, the system 10 also includes a controller 110 and one or more hydrostatic pressure transducers 122, 124 and 126. As illustrated, transducer 122 is located within vessel 46 at local region 50, transducer 124 is located outside vessel 46 but at local region 50, and transducer 126 is located at the target tissue site 52, for example, within tumor T.

Controller 110 generates pump control signals for the respective pumps 2 and 32. The controller 110 may be responsive to a pressure detector 120 and one or more of pressure transducers 122, 124 and 126 to generate control signals for pump 32 which is responsive to and representative of the difference between the hydrostatic pressure at the local region 50 and the hydrostatic pressure at the target tissue site 52. The pump 32 is selectively operable in a pulsatile manner at a desired repetition rate, so that pulsatile amounts of a hydrostatic pressure increasing agent from P/M agent reservoir 30 is infused into vessel 44. With this feedback configuration, pump 32 delivers the agent from P/M agent reservoir 30 to the local region 50 in amounts related to the difference in hydrostatic pressures.

In another embodiment, controller 110 may be responsive to the transducer 122 only to generate a control signal for P/M agent pump 32, which is a local pressure signal representative of the hydrostatic pressure at the local region 50. In this form, the system 10 operates on the basis that the pressure at the site 52 remains substantially constant, and thus the local region pressure alone is representative of the pressure differential of interest. In all of these embodiments, T/D agent pump 22 may be operated in a pulsatile manner, as described, or alternatively, may provide infusion at a constant rate while only P/M agent pump 32 operates in a pulsed manner.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of enhancing delivery of a pharmaceutical formulation to a target tissue site in a mammal, comprising the steps of:

A. delivering the pharmaceutical formulation to a region near said target tissue site, B. establishing a transient repetitive pulsatile pressure differential between said region near said target tissue site and said target tissue site, and in response thereto, transport of said pharmaceutical formulation from said region near said target tissue site toward said target tissue site.

2. The method of claim 1 wherein said establishing step includes sub-step of establishing a repetitive pressure increase at said region.

3. The method of claim 2 wherein said establishing step B includes the sub-step of administering an agent into the mammal at said region on a repetitive pulsatile basis, said agent being capable of establishing an increase in hydrostatic pressure in the mammal at the locus of said agent.

4. The method of claim 3 wherein administering step A includes the sub-step of infusion of said pharmaceutical formulation on a repetitive pulsatile basis, wherein said periodic pulsatile infusion of said pharmaceutical formulation is synchronous with said periodic repetitive infusion of said agent.

5. The method of claim 4 wherein the repetition rate of said pulsatile infusion of said agent is constant.

6. The method of claim 4 wherein the repetition rate of said pulsatile infusion of said agent is irregular.

7. The method of claim 3 wherein the formulation and the agent are delivered by systemic intravenous injection.

8. The method of claim 7 wherein the formulation comprises an antibody.

9. The method of claim 8 wherein said target tissue site is a tumor or a lymph node.

10. The method of claim 9 wherein the repetition rate of said pulsatile administration of said agent is constant.

11. The method of claim 9 wherein the repetition rate of said pulsatile administration of said agent is irregular.

12. The method of claim 3 wherein the repetition rate of said pulsatile administration of said agent is constant.

13. The method of claim 3 wherein the repetition rate of said pulsatile administration of said agent is irregular.

14. The method of claim 2 wherein the formulation is delivered by systemic intravenous injection.

15. The method of claim 14 wherein said tissue site is a tumor or a lymph node.

16. The method of claim 15 wherein the repetition rate of said pressure differential is constant.

17. The method of claim 15 wherein the repetition rate of said pulsatile pressure differential is irregular.

18. The method of claim 2 wherein said region is intravascular.

19. The method of claim 18 wherein said target tissue site is extravascular.

20. The method of claim 19 wherein said target tissue site is a tumor or a lymph node.

21. The method of claim 20 wherein the repetition rate of said pulsatile pressure differential is constant.

22. The method of claim 20 wherein the repetition rate of said pulsatile pressure differential is irregular.

23. The method of claim 2 wherein the repetition rate of said pulsatile pressure differential is constant.

24. The method of claim 2 wherein the repetition rate of said pulsatile pressure differential is irregular.

25. The method of claim 1 wherein said establishing step includes the sub-step of establishing a repetitive pressure decrease at said target tissue site.

26. A method of enhancing delivery of a pharmaceutical formulation to a target tissue site in a mammal, comprising the steps of: delivering the pharmaceutical formulation to a region near said target tissue site; establishing a transient repetitive pressure differential between said region near said target tissue site and said target tissue site, and in response thereto, transport of said pharmaceutical formulation from said region near said target tissue site toward said target tissue site.

27. The method of claim 26, wherein the pharmaceutical formulation comprises a therapeutic agent.

28. The method of claim 27, wherein the therapeutic agent comprises a monoclonal antibody.

29. The method of claim 28, wherein the target tissue site is a tumor.

30. The method of claim 28, wherein the region is a lymph node.

31. The method of claim 26, wherein the pharmaceutical formulation comprises a diagnostic agent.

32. The method of claim 31, wherein the diagnostic agent comprises a monoclonal antibody.

33. The method of claim 32, wherein the target tissue site is a tumor.

34. The method of claim 32, wherein the region is a lymph node.

35. An apparatus for administering a pharmaceutical formulation to a target tissue site in a mammal, comprising:
    A. a first reservoir for storing said pharmaceutical formulation,
    B. a second reservoir for storing an agent capable of establishing an increase in hydrostatic pressure in the mammal at the locus of said agent in the mammal,
    C. an agent pump including means for delivering said agent from said second reservoir to a region near the target tissue site on a repetitive pulsatile basis, and
    D. a pharmaceutical formulation pump including delivery means for delivering said pharmaceutical formulation from said first reservoir to said region near the target tissue site.

36. An apparatus according to claim 35 further comprising:
    E. control means for generating a pharmaceutical formulation pump control signal representative of the difference between the hydrostatic pressure at said region and the hydrostatic pressure at said target tissue site, and wherein said pharmaceutical formulation pump is selectively operable in response to said pharmaceutical formulation control signal and said delivery means delivers said pharmaceutical formulation from said first reservoir to said region in amounts related to said difference.

37. An apparatus according to claim 36 wherein said control means includes:
    i. a first sensing means for generating a local pressure signal representative of said hydrostatic pressure at said region,
    ii. a second sensing means for generating a tissue pressure signal representative of said hydrostatic pressure at said target tissue site, and
wherein said control means is responsive to said local pressure signal and said tissue pressure signal to generate said pharmaceutical formulation pump control signal.

38. An apparatus according to claim 36 wherein said control means includes:
    a first sensing means for generating a local pressure signal representative of said hydrostatic pressure at said region, and wherein said control means is responsive to said local pressure signal to generate said pharmaceutical formulation pump control signal.

* * * * *